United States Patent [19]
Svara et al.

[11] Patent Number: 4,885,394
[45] Date of Patent: Dec. 5, 1989

[54] PROCESS FOR THE PREPARATION OF TERTIARY PHOSPHINE OXIDES

[75] Inventors: Jürgen Svara, Cologne; Norbert Weferling, Hürth, both of Fed. Rep. of Germany

[73] Assignee: Hoechst Aktiengesellschaft, Frankfurt am Main, Fed. Rep. of Germany

[21] Appl. No.: 258,691

[22] Filed: Oct. 17, 1988

[30] Foreign Application Priority Data

Nov. 7, 1987 [DE] Fed. Rep. of Germany ....... 3737938

[51] Int. Cl.$^4$ ................................................ C07F 9/02
[52] U.S. Cl. ............................................ 568/14; 568/8
[58] Field of Search ...................................... 568/14, 8

[56] References Cited

U.S. PATENT DOCUMENTS 4,096,189  6/1978  Staendeke .
4,324,919  4/1982  Elsner et al. .
4,618,719  10/1986  Bay et al. ................................ 568/8

Primary Examiner—John Doll
Assistant Examiner—Stuart L. Hendrickson

[57] ABSTRACT

The invention relates to a process for the preparation of tertiary phosphine oxides by reacting primary or secondary phosphines with dimethyl carbonate under elevated pressure at elevated temperature.

4 Claims, No Drawings

PROCESS FOR THE PREPARATION OF TERTIARY PHOSPHINE OXIDES

The present invention relates to a process for the preparation of tertiary phosphine oxides of the general formula $$(CH_3)_n R_{3-n} P=O \qquad (I)$$

in which R denotes linear or branched alkyl, alkenyl, cyclic or polycyclic alkyl or alkenyl, arylalkyl or alkylaryl groups having 1 to 24 carbon atoms, and n denotes an integer from 1 to 3.

Tertiary phosphine oxides are becoming increasingly important in industry as emulsifiers or agents for surface-treatment of metals, and also as extractants for organic substances or in hydrometallurgy. There has, therefore, been no lack of attempts hitherto to find methods of preparation of these compounds.

Thus, it is known to prepare tertiary phosphine oxides, for example, by oxidation of tertiary phosphines, by thermal decomposition of quaternary phosphonium hydroxides or by alkaline hydrolysis of quaternary phosphonium halides (G. M. Kosolapoff/L. Maier: Organic Phosphorus Compounds, Vol. 3, Wiley-Interscience, New York (1972)). Other processes use the reaction of phosphorus halides with organometallic compounds or the adduction of olefins, aldehydes or ketones with primary or secondary phosphine oxides.

These processes have the disadvantage that their conversion to an industrial scale is scarcely practicable or that they are based on starting compounds whose preparation proceeds via several process steps and is therefore very expensive.

Surprisingly, a novel route has now been found which results in the phosphine oxides described initially in one step, in high yield and in high purity.

In detail, this process according to the invention comprises reacting primary or secondary phosphines of the general formula $$R_{3-n} PH_n \qquad (II)$$

in which R has the abovementioned meaning and n denotes 1 or 2, with dimethyl carbonate under elevated pressure at elevated temperature.

The reaction is advantageously carried out at a temperature from 150° to 250° C. and at a pressure from 2 to 100 bar.

It is advisable to employ at least 1 mole of dimethyl carbonate per P-H function to be alkylated.

The reaction can be carried out without solvent or, in a favorable manner, in an excess of dimethyl carbonate. However, it is also poossible to employ customary organic solvents, such as methanol or toluene.

After releasing and burning the gaseous by-products, the reaction product can be isolated, for example, by fractional distillation of the residue, it being possible to recover and feed to the next batch the excess dimethyl carbonate.

If required by the physical properties of the product, work-up can also take place by another method known to those skilled in the art, such as, for example, by crystallization or sublimation.

Reactions of primary and secondary phosphines with organic carbonates are rarely described in the literature, and those with dimethyl carbonate not at all. It is known that dibutylphosphine reacts with cyclic carbonates (ethylene carbonate, propylene carbonate, vinylene carbonate) to form bridged, tertiary alkylene-bis(phosphine oxides) (Keough, P. T.; Grayson, M.; J. Org. Chem. 1962, 27, 1817).

The essence of the present invention is described in greater detail by the examples below.

EXAMPLES

Primary or secondary phosphine and dimethyl carbonate, and also, if required, a solvent, are introduced into a 500 ml laboratory autoclave under a protective gas ($N_2$ or Ar) and heated while stirring using a magnetic stirrer. Commencement of the reaction is indicated by an increase in the internal pressure. When the reaction is complete, the autoclave is cooled and the gaseous by-products released via a combustion tube. The liquid residue is subjected to distillation, unreacted dimethyl carbonate being obtained at atmospheric pressure and the tertiary phosphine oxide generally under reduced pressure. In the case of high-melting products, the solid residue is sublimited after removing low-boiling products.

The reaction conditions in each case can be seen from the table below.

TABLE

| Product | Phosphine [g] ([mmol]) | Dimethyl-carbonate [g] ([mmol]) | Bath temp. [°C.] | Reaction time [h] | Final pressure [bar] | Conversion [%] | Yield[2] [g] ([%]) | Boiling point [°C.] ([mbar]) | [31]p-NMR [ppm] |
|---|---|---|---|---|---|---|---|---|---|
| $\underset{C_4H_9P(CH_3)_2}{\overset{\overset{\displaystyle O}{\|\|}}{}}$ | sec-butylphosphine 90,1 (1000) | 270,2 (3000) | 225 | 11 | 49 | 66 | 38,3 (29) | 98 (1) | 46,4 |
| $\underset{C_8H_{17}P(CH_3)_2}{\overset{\overset{\displaystyle O}{\|\|}}{}}$ | n-octylphosphine 37,8 (259) | 117,6 (1306) | 220 | 3 | 31 | 77 | 33,1 (67) | 145 (1) | 45,7 |
| $\underset{C_{16}H_{33}P(CH_3)_2}{\overset{\overset{\displaystyle O}{\|\|}}{}}$ | hexadecylphosphine 86,0 (333) | 120,0 (1332) | 225 | 5 | 51 | 100 | 74,3 (74) | 173 (0,3) | 41,6 |
| $\underset{(C_4H_9)_2PCH_3}{\overset{\overset{\displaystyle O}{\|\|}}{}}$ | di-n-butylphosphine 54,1 (370) | 83,3 (925) | 230 | 6 | 27 | 100 | 41,7 (64) | 120–130 (1) | 46,3 |
| $\underset{(C_6H_{11})_2PCH_3}{\overset{\overset{\displaystyle O}{\|\|}}{}}$ | dicyclohexylphosphine 119,1 (602) | 108,4 (1203) | 230 | 4 | 48 | 95 | 94,2 (79) | 135 (1) | 50,6 |

TABLE-continued

| Product | Phosphine [g] ([mmol]) | Dimethyl-carbonate [g] ([mmol]) | Bath temp. [°C.] | Reaction time [h] | Final pressure [bar] | Conversion [%] | Yield[2] [g] ([%]) | Boiling point [°C.] ([mbar]) | $^{31}$p-NMR [ppm] |
|---|---|---|---|---|---|---|---|---|---|
| 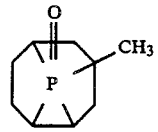 | 9-phosphabicyclo-[3,3,1]- and[4,2,1]-nonane[1] 73,3 (515) | 92,8 (1030) | 220 | 19 | 51 | 100 | 69,8 (78) | 120 (1)[3] | 65,8/ 39,9 |

[1] isomer mixture
[2] relative to the amount employed
[3] product is sublimed

We claim:

1. A process for the preparation of tertiary phosphine oxide of the general formula $$(CH_3)_n R_{3-n} P=O \qquad (I)$$

in which R is a member selected from the group consisting of linear alkyl, branched alkyl, alkenyl, cyclic alkyl, polycyclic alkyl, polycyclic alkenyl, arylalkyl, and alkylaryl groups having from 1 to 24 carbon atoms, and n stands for 1 or 2, which comprises reacting phosphine of the general formula

(II)

in which R has the meanings given above and $R_1$ is a member selected from the group consisting of hydrogen, linear alkyl, branched alkyl, alkenyl, cyclic alkyl, polycyclic alkyl, polycyclic alkenyl, aryalkyl, and alkylaryl groups having from 1 to 24 carbon atoms, with dimethyl carbonate under pressure from 2 to 100 bar and a temperature from 150° to 250° C.

2. The process as claimed in claim 1, wherein the reaction is carried out in an organic solvent.

3. The process as claimed in claim 1, wherein at least 1 mole of dimethyl carbonate is employed per P-H function to be alkylated.

4. The process as claimed in claim 1, wherein the reaction is carried out in an excess of dimethyl carbonate.

* * * * *